United States Patent [19]
Stewart et al.

[11] Patent Number: 5,882,590
[45] Date of Patent: Mar. 16, 1999

[54] MONITORING AND CONTROL OF STERILIZATION PROCESSES WITH SEMICONDUCTOR SENSOR MODULES

[75] Inventors: Bonnie Stewart, Durham; Peter E. Zell, Raleigh, both of N.C.

[73] Assignee: American Sterilizer Company, Mentor, Ohio

[21] Appl. No.: 675,743

[22] Filed: Jul. 3, 1996

[51] Int. Cl.⁶ .............................. A61L 2/00; G05D 7/00; G05D 16/00; G05B 1/00
[52] U.S. Cl. ........................... 422/28; 422/110; 422/108; 422/105; 422/32
[58] Field of Search .............................. 422/28, 110, 108, 422/105, 32, 111, 298, 305

[56] References Cited

U.S. PATENT DOCUMENTS

| | | | |
|---|---|---|---|
| 4,908,188 | 3/1990 | Jeffries | 422/111 |
| 5,608,156 | 3/1997 | Ando et al. | |

FOREIGN PATENT DOCUMENTS

| | | |
|---|---|---|
| 0 467 479 A1 | 7/1991 | European Pat. Off. |
| 1425685 | 8/1973 | United Kingdom |
| 2 165 948 | 10/1984 | United Kingdom |
| 2 191 585 | 1/1987 | United Kingdom |

*Primary Examiner*—Lynette F. Smith
*Attorney, Agent, or Firm*—Fay, Sharpe, Beall, Fagan, Minnich & McKee

[57] ABSTRACT

The invention is a system and method for real-time monitoring and control of chemical sterilant concentration during all phases of a sterilization cycle by employing semiconductor-based sensor modules to selectively detect and measure the actual sterilant concentration in real time. In response to the transmitted concentration values, the sterilizer control system controls critical environmental parameters to maintain concentration levels within acceptable ranges for given time periods to assure sterilization efficacy and that the sterilant has been properly exhausted at completion of the cycle. The selectivity, sensitivity and accuracy of the semiconductor sensor are optimized by calibrating the sensor to baseline environmental parameters and by adjusting the sensor concentration reading when environmental parameters change during the sterilization cycle, by programming a new baseline value for the sterilant concentration at the new condition.

24 Claims, 2 Drawing Sheets

MONITORING AND CONTROL OF STERILIZATION PROCESSES WITH SEMICONDUCTOR SENSOR MODULES

BACKGROUND OF THE INVENTION

In systems for sterilization and decontamination, certain critical process parameters must be maintained within acceptable limits for a given period of time in order to achieve target sterility assurance levels. Real time monitoring and control methods for such critical parameters as temperature, pressure and time are widely known and practiced. However, in liquid and gas chemical sterilization and decontamination systems, the critical parameter of sterilant concentration must also be monitored and controlled. Until the present invention, there has been no practical method for directly measuring the sterilant concentration in real time that is economically feasible for use in all types of sterilization and decontamination systems.

Indirect methods to measure the concentration of chemical sterilants, such as ethylene oxide, formaldehyde, hydrogen peroxide and peroxygen compounds are commonly employed. For example, the theoretical concentration of vaporized hydrogen peroxide in a sterilization chamber at any given time may be calculated by correlating the consumption of liquid peroxide supplied to the vaporization system with such system parameters as temperature, pressure, relative humidity, dew point and, if applicable, air flow rate and chamber volume. Based on this indirect calculation, the sterilizer control system may then operate various sterilizer components, such as pumps, valves, etc., to control the amount of liquid hydrogen peroxide delivered to the vaporizer in order to maintain the desired theoretical concentration of sterilant gas/vapor in the chamber, while avoiding condensation due to vapor saturation.

It is known, however, that for most chemical sterilant systems there may be a disparity between the theoretical sterilant concentration and the actual sterilant concentration due to variable environmental factors, including decomposition, absorption and/or adsorption of the sterilant gas/vapor upon contact with various surfaces within the system and the load being processed. The effect of these factors on the actual sterilant concentration is unpredictable and varies from load to load and system to system such that adjusting the supply of liquid chemical sterilant to account for these effects is impractical and inefficient. To assure that target sterility assurance levels have been met, therefore, a system for direct, real time measurement of the actual chemical sterilant concentration in the chamber at any given time is preferred.

Recently, developments in near infrared spectrophotometry have allowed the use of this technology to directly measure and control the concentration of hydrogen peroxide vapor in a given sterilization or decontamination environment in real time. Such a system is disclosed in our commonly assigned, copending U.S. patent application Ser. No. 08/508,314, filed Jul. 27, 1995, the disclosure of which is hereby incorporated by reference. This approach, while demonstrated to be effective, is costly and may appreciably add to the overall cost of sterilization and decontamination systems. In addition, the large overall size of the near infrared system, as currently configured, precludes easy integration into small sterilizer or decontamination systems, such as small endoscope or dental instrument sterilizers.

There remains a need for a practical and reliable system that provides real-time monitoring and control of the actual concentration of liquid or gas chemical sterilants during a sterilization or decontamination cycle and that can be inexpensively and easily integrated into virtually any system. There is also a need for a system that is highly selective for and sensitive to the chemical sterilant of choice.

A known and relatively inexpensive technology for selectively measuring concentrations of gases and/or liquids employs semiconductor-based sensors. Semiconductor technology has been used for detecting and warning of toxic and/or explosive gases in domestic and industrial environments. For example, semiconductor-based sensors have been used to detect gases in the cabs of motor vehicles, and to produce signals or control outputs for the switching on or off of air filtering systems or ventilation systems if the gas concentration reaches a predetermined set-point concentration. Semiconductor monitoring systems have been used for detection of ethylene oxide in areas around sterilizers on a continuous, 24-hour air sampling basis. Semiconductor sensor probes have also been used to detect the constituents and concentrations of gases, such as carbon monoxide, oxides of nitrogen, and hydrocarbons in exhaust gases from internal combustion engines. Other such sensors have variously been used to sense the presence and/or concentrations of gases and liquids, such as ethanol, carbon dioxide, glutaraldehyde and ammonia.

A known problem with semiconductor-based systems is their sensitivity to environmental conditions. For example, variations in temperature, relative humidity, and/or flow velocities of air currents that are to be monitored can affect the stability and accuracy of the semiconductor sensor signal and produce erroneous gas concentration readings. Moreover, semiconductor sensors may demonstrate changes in electrical conductivity in the presence of oxygen and oxidizing gases other than the gas being measured. Variations in these environmental conditions during a sterilization cycle and between cycles, often in combination with variations in pressure, are present in virtually all sterilization and decontamination systems employing liquids and gases, such as ethylene oxide, peroxygen compounds, formaldehyde, hydrogen peroxide, and the like. Thus, until the present invention, semiconductor-based sensors have not been described for real-time monitoring of the concentration of sterilant liquid or gas within a sterilization chamber during a decontamination or sterilization cycle.

SUMMARY OF THE INVENTION

The present invention is a system and method employing sensors based on semiconductor technology to provide real-time direct measurement and control of the actual concentration of a chemical sterilant liquid or gas in a sterilization or decontamination system during a sterilization cycle. Although the terms "decontamination" and "sterilization" may be used interchangeably in this specification, the system and method of the present invention are applicable to all levels of biological contamination control, whether referred to as sterilization, decontamination, disinfection, sanitization, or otherwise. The term "sterilant" is intended to include all liquid and gas sterilization, decontamination, disinfection, sanitization agents, as understood by those skilled in the art.

According to the invention, the sterilant concentration is monitored and controlled in real time during all phases of a sterilization cycle in order to maintain concentration levels within acceptable ranges for given time periods to assure that critical concentration parameter values have been met, sterilization efficacy has been achieved, and the sterilant has been properly exhausted upon completion of the cycle.

Thus, the invention overcomes the previous problem of a dichotomy between indirectly calculated concentration values and the actual concentration values due the decomposition, absorption, adsorption, and other uncontrolled effects on the sterilant concentration. Further, the compact size and the low cost of the semiconductor sensing module allows inexpensive and efficient integration into virtually any sterilization system.

By the invention, a semiconductor-based sensor probe comprising a sensing element having a measurable electrical characteristic is positioned in fluid communication with a sterilant, in a sterilizing system, for sensing a baseline concentration of the sterilant at a given set of environmental parameter values. A receiving unit is programmed to store the electrical characteristic value as representative of the baseline concentration of the sterilant.

When the concentration of the sterilant changes during a sterilization cycle, a change in the electrical characteristic of the sensing element is detected in real time by the receiving unit, which then transmits the value representing the new sterilant concentration to a sterilizer control system. The sterilizer control system is programmed to store a predetermined reference sterilant concentration range at the first set of environmental parameter values. The sterilizer control system is further programmed to receive the new concentration value and to compare the new value to the stored reference concentration range. When the new concentration value falls within the reference concentration range, the sterilizer control system indicates acceptable sterilization conditions. When the new concentration value falls outside the reference concentration range, the sterilizer control system sends a signal to a process control unit to adjust the amount of sterilant delivered to and/or exhausted from the sterilization system, or to adjust an environmental parameter value. Preferably, the sterilant concentration is controlled and maintained within the reference sterilant concentration range for a period of time sufficient to achieve sterilization.

To assure the accuracy of the sensor for the sterilization application for which it is to be used, the sensor baseline reading is preferably calibrated according to initial cycle parameters including, but not limited to, temperature, pressure, relative humidity and, if applicable, air flow velocity, oxidizing substance concentration, and combinations of these. During the sterilization cycle, the sterilizer control system is programmed to monitor these environmental parameters and, when one or more of the parameters changes, to signal the receiving unit to adjust the sensor system by recognizing and storing a new baseline value for the sterilant concentration at the new condition. Thus, the sensor-based monitoring and control system may be used, and calibrated for, virtually every sterilization cycle involving liquid and gas sterilants.

Preferably, an additional sterilant sensor module is positioned exteriorly to the sterilizer to detect sterilant gas in the environment near the sterilizer. When the detected gas exceeds a predetermined limit, the sterilizer control system signals the process control system to stop the sterilization cycle and/or to exhaust sterilant from the system.

Suitable sterilants that may be employed in the monitoring and control system of the present invention include any liquid or gas sterilant that is detectable by a semiconductor sensing system including, but not limited to, ethylene oxide gas, liquid and gaseous hydrogen peroxide, liquid and gaseous formaldehyde, liquid and gaseous peroxygen compounds, ozone, alcohol, glutaraldehyde, ammonia, and mixtures of these.

The semiconductor sensor of the invention is of an appropriate size and configuration to fit virtually all sterilizer systems. A preferred semiconductor sensing system is inexpensive compared to currently available systems for measuring sterilant concentrations and demonstrates high reliability and high selectivity for and sensitivity to each sterilant employed.

DETAILED DESCRIPTION OF THE INVENTION

Figure 1:
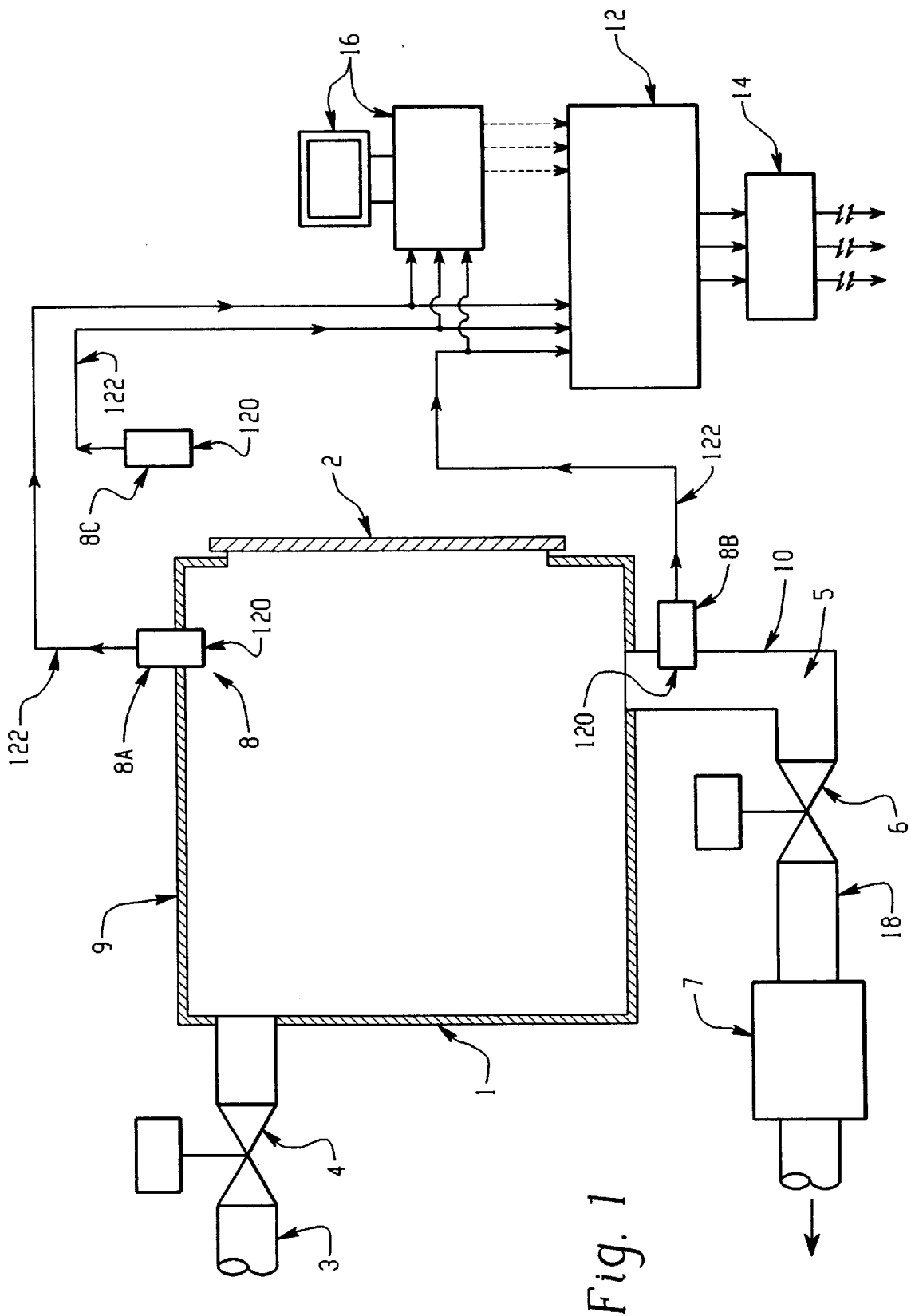
FIG. 1 is a schematic representation of a typical sterilization system employing the semiconductor sensor modules of the invention.

The present invention is concerned with the real-time monitoring and control of the sterilant concentration during all phases of a sterilization cycle in order to maintain the concentration levels within acceptable ranges for given time periods to assure that critical concentration parameter values have been met, sterilization efficacy has been achieved, and the chamber has been properly exhausted at the end of the cycle. By the invention, the concentration of liquid and/or gas sterilants during the cycle is measured by a semiconductor-based sensor in fluid communication with the sterilant.

The sensor module has a sensing element and integrated electronics that react to changes in the concentration of certain chemicals to which the element is exposed. The electronics and the software associated with the module can be configured to react to a target chemical compound. Any semiconductor-based sensor module, and its associated software, that is selective for and sensitive to the particular liquid or gas used as the sterilant may be adapted for use in the invention. For example, a suitable sensor module for detecting and measuring concentrations of ethylene oxide gas is the EtO Model 300 Gas Monitoring System in combination with Intellisense software, "Matrix Fingerprinting Technology", both manufactured by Air Purification Laboratories, Lexington, Ky. Sensor modules and associated software for glutaraldehyde, ammonia, carbon monoxide, carbon dioxide, hydrogen, alkanes, alcohols and liquid hydrogen peroxide are also available from Air Purification Laboratories. However, these and other similar gas or liquid detection sensor systems are typically manufactured for use as environmental air or liquid sampling devices and, therefore, must be adapted for use in the sterilization systems according to the system and method of the present invention.

A particular feature of the invention is that the stability and sensitivity, and thus the accuracy, of the sensor sterilant concentration measurements are optimized for differing environmental conditions encountered in different sterilization systems. For example, sterilization systems employing ethylene oxide gas or hydrogen peroxide vapor involve different temperatures, pressures, relative humidities, and/or air flow velocities. In addition, some sterilization systems may include the presence of oxidizing substances, other than the sterilant to be measured, that may affect the electrical conductivity or resistance of the probe. Further, environmental conditions, such as relative humidity, temperature and pressure, may change dramatically during a single sterilization cycle. Such sterilization cycles include, but are not limited to, those employing deep vacuums with or without admission of air during the cycle, flow-through systems at near atmospheric pressure, and combinations of these, and other systems that are known in the art. Virtually every sterilization system also employs a cycle phase wherein the sterilant is exhausted from the sterilizer after the exposure phase and may include aeration of the sterilizer.

To assure the accuracy of the sensor in measuring the concentration of the sterilant during all sterilization cycle phases, the sensor is preferably initially calibrated for the sterilization application for which it is to be used according to the initial cycle parameters in the sterilization chamber including, but not limited to, temperature, pressure, relative humidity and, if applicable, the presence and/or flow of air or the presence of other oxidizing gases in the system. Thus, the sensor-based monitoring and control system may be used, and calibrated for, virtually every sterilization cycle involving liquid and gas sterilants. To assure the accuracy of the sterilant concentration measurement throughout changing environmental conditions during a sterilization cycle, the sterilizer control system is programmed to monitor the environmental parameters and, if one or more of the environmental parameters changes, to signal the sensor module electronics and software to recognize and program a new baseline value for the sterilant concentration at the new condition. As discussed below, the baseline value is preferably readjusted in response to pressure changes within the sterilization system.

Reference will now be made in detail to the preferred embodiments of the invention, an example of which is illustrated in the accompanying drawings. As illustrated in FIG. 1, a typical sterilization system employing vapor hydrogen peroxide or ethylene oxide gas sterilant comprises a sterilization or decontamination enclosure or chamber 1 having a sealable door 2, a sterilant supply inlet line 3, a sterilant inlet valve 4, a chamber drain line or exhaust outlet line 5, and a chamber outlet valve 6 typically connected to a vacuum pump 7. Although the schematic represents an ethylene oxide or hydrogen peroxide gas sterilization system, a liquid or other gas sterilization system could be represented differently without departing from the spirit of the invention. A semiconductor-based sensor module 8 or a plurality of sensor modules 8A, 8B may be located within the chamber or removably connected to a chamber wall 9 or chamber drain/exhaust outlet wall 10 with the sensor in fluid contact with sterilant in the chamber 1 to measure the concentration of the sterilant in the chamber. Sensor modules (not shown) may additionally or alternatively be located in another area of the sterilization system, such as in a line 3 leading to the sterilant supply inlet valve 4 or in a line 18 leading from the outlet valve 6. A single semiconductor module in fluid communication with the sterilant is sufficient to provide real time sterilant concentration values. As described below, it is sufficient that the sensing element alone be in fluid communication with the sterilant, such that the remainder of the sensor module may be interior or exterior to the chamber.

In another embodiment of the invention, disclosed in our commonly assigned, copending U.S. patent application Ser. No. 08/602,515, filed Feb. 16, 1996 now U.S. Pat. No. 5,788,925, the disclosure of which is hereby incorporated by reference, the sterilant concentration sensing element of the sensor module may be located in a load-simulation device for real time monitoring and control of the concentration of a sterilant in a load and for parametric release of the load when the sterilization parameters, including sterilant concentration have been met. When employing liquid sterilants, such as aqueous hydrogen peroxide, as a source of a gas sterilant, it may also be desirable to employ a sensor module to determine the actual concentration of the liquid sterilant being delivered to the means for generating the gas sterilant.

Preferably, an additional semiconductor-based sensor module 8C is located exteriorly to the sterilization system to sense the presence of and concentration of a gas sterilant in the environment around the sterilization system, and to provide for audible and visual alarms if predetermined gas limits are exceeded in this area. As described below, the external sensor module 8C is in electronic communication with a sterilizer control 12 which signals a process control unit 14 to operate valves, pumps, etc. to shut off the sterilant delivery line 3 and/or exhaust sterilant from the sterilization system if predetermined gas limits are exceeded.

The sterilization system illustrated in FIG. 1 also includes sensors (not shown) for measurement of system environmental parameters, such as resistance temperature detectors (RTDs) for temperature monitoring, pressure transducers for pressure monitoring, humidity sensors for monitoring relative humidity and air velocity meters for measuring air flow rates. The preferred locations for the environmental parameter sensors and sterilant concentration sensor modules in any particular sterilization system are dependent on the sterilization system employed and are known to those skilled in the art.

Figure 2:
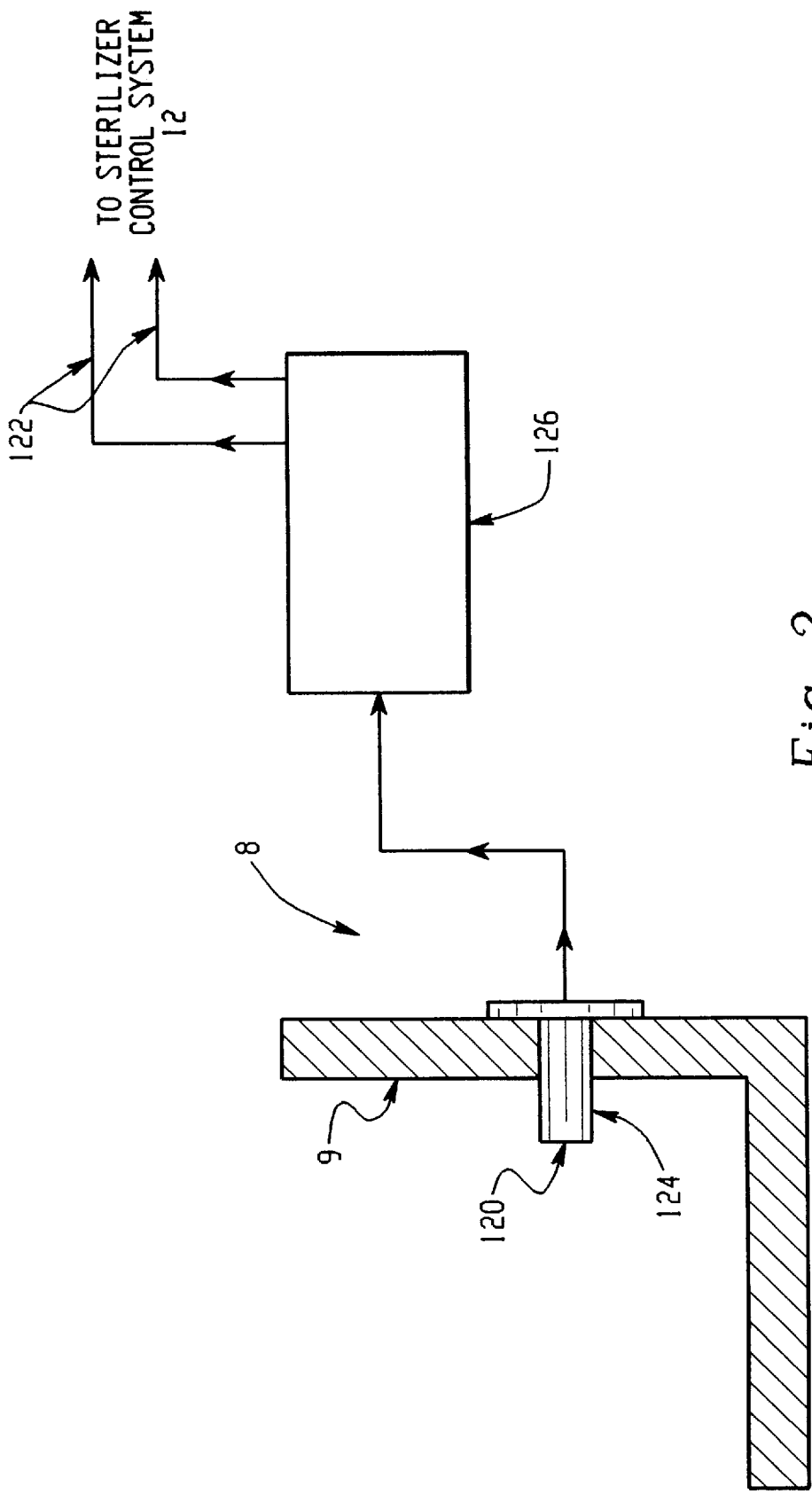
FIG. 2 is a schematic representation of a semiconductor module employed in the invention.

As illustrated in FIGS. 1 and 2, each semiconductor-based sensor module 8 has a sensing end 120 that comprises a sensing element 124 of a chemical composition that is selected based on the particular sterilant liquid or gas to be detected in a particular sterilization system. When in fluid contact with the sterilant under a given set of environmental conditions (i.e. the parameters of temperature, pressure, relative humidity, air flow, etc.), the sensing element 124 exhibits a particular electrical characteristic, such as conductivity, capacitance or resistance, that is measurable. Assuming that the environmental parameter values do not change, a change in the electrical characteristic of the sensing element indicates a concomitant, reliably measurable change in sterilant concentration.

The sensor module 8 also comprises a receiving unit 126 electronically connected to the sensing element 124 for receiving the electrical characteristic value and for detecting in real time a change in the electrical characteristic value as an indication of a proportional change in sterilant concentration. The receiving unit 126 comprises electronics and software to receive and analyze an electronic signal from the sensing element 124 and to convert the signal into an analog signal for transmission, via a transmitting unit 122, to a sterilizer control system 12. Thus, the electrical signal from the sensor module 8 that is indicative of the sterilant concentration under a given set of environmental conditions is transmitted to the sterilizer control system 12 as an analog output signal, which may be in milliamperes or volts.

The transmitted signal is read by the sterilizer control system 12 which then sends an input signal to a process control system 14. Based on this input signal, the process control system 14 provides output instructions to operate electrically operated valves, pumps, etc., which in turn control various phases of the sterilization cycle, including delivery of liquid or gas sterilant during the exposure phases and/or removal of the sterilant during exhaust or purge phases. In the case of the environmental sensor monitor 8C, the process control system 14 is preferably programmed to control various air handling and ventilation systems to clear the environment of the noxious gases and, more preferably, to respond by preventing further delivery of sterilant to the system and/or by exhausting sterilant from the system.

The sterilizer control system 12 may be any system including, but not limited to, a microprocessor or a logic circuit that is programmed to receive the sensed sterilant concentration value and also to control the value of the sterilant concentration in real time during the sterilization cycle by governing the process control unit 14. Thus, predetermined target processing conditions inside the sterilization system may be maintained during all phases of the sterilization cycle, including the exposure to sterilant phase and the exhaust/purge phase.

In a typical sterilization cycle employing the sterilant concentration real time monitoring and control system of the invention, the sensing element 124 is positioned in a sterilizer 1 for sensing a baseline concentration of the sterilant at a first set of environmental parameter values. The sensing element 124 has a baseline electrical characteristic value at the baseline concentration. The receiving unit 126, electronically connected to the sensing element 124 is programmed to store the baseline electrical characteristic value and to detect in real time a change in that value, as the sterilization cycle proceeds, as an indication of a new sterilant concentration at the first set of environmental parameter values. The new value of the sterilant concentration is transmitted in real time to the sterilizer control system 12 via the transmitting unit 122. The sterilizer control system 12 is programmed to store a predetermined reference sterilant concentration range at the first set of environmental parameter values. The sterilizer control system is further programmed to receive the new sensed concentration value and to compare that value to the stored reference concentration range, and to indicate acceptable sterilization conditions when the new value falls within the reference range, and to signal the process control unit 14 to change the sterilant concentration when the new value falls outside the reference concentration range.

As described above, when an environmental condition in the sterilization system changes during a sterilization cycle, the sensor module 8 must be adjusted to assure the accuracy of the sterilant concentration reading. Thus, by the invention, the sterilizer control system 12 is preferably further programmed to monitor the set of environmental parameter values during the cycle and, when a parameter value changes, to signal the receiving unit 126 to adjust the sensor system by recognizing and storing a new baseline sterilant concentration value at the new set of environmental parameter values. For example, in a sterilization system employing vapor hydrogen peroxide as the sterilant in a vacuum chamber, the sensor system is initially set with respect to the temperature, pressure and relative humidity of the chamber at the beginning of a cycle. Hydrogen peroxide vapor is introduced into the chamber, producing a slight rise in pressure. A real time measurement of the concentration of the vapor is determined and transmitted to the sterilizer control system. After a hold period, air is introduced into the chamber and the pressure in the chamber rises. Pressure transducers in the chamber transmit the rise in pressure value to the sterilizer control system which then sends a signal to the receiving unit 126 to establish a new baseline for the sterilant concentration reading at the new pressure level.

Preferably, the sterilant concentration is monitored and controlled in real time during the sterilization cycle to maintain a concentration that falls within the predetermined sterilant concentration range for a period of time sufficient to achieve sterilization.

During the exhaust/aeration phase of a cycle, the sensor module 8 continues to provide real time monitoring of the sterilant concentration, and the sterilizer control system 12 continues to signal the process control unit 14 to operate valves, pumps, etc., to exhaust and/or aerate the system until all the sterilant is removed from the sterilizer or is at an acceptable level to end the sterilization process. During the aeration phase of the sterilization cycle, the pressure in the chamber typically alternates between deep vacuum and pressure rises due to admission of air. To obtain a real time sterilant concentration reading under these conditions requires frequent adjustment of the sensor system baseline reading.

To monitor and control the concentration of the sterilant in the immediate environment exterior to the sterilizing system, an additional exterior sensor probe 8C is provided. The sensing element of this probe is in electronic communication with the receiving unit and the external sterilant concentration is transmitted to the sterilizer control system through the transmitting unit. The sterilizer control system is programmed to store a predetermined sterilant concentration limit value and to signal the process control system to stop the sterilization cycle and/or exhaust sterilant from the sterilizer when the external concentration value exceeds the predetermined limit value.

In another embodiment of the invention, the semiconductor sensor module transmitting unit 122 transmits an analog signal representing the sterilant concentration value in real time to an external microprocessor 16 intermediate to the sterilizer control system 12. Such an intermediate processor 16 preferably has the capability of data storage, data display, and alarm capabilities separate from the sterilizer control system 12. Data from the intermediate processor may then be sent to the sterilizer control system and also may be retained as a permanent record of sterilization parameters throughout the sterilization process.

The method of the invention proceeds by the steps of exposing the sensing element of the sensor probe to the sterilant during a sterilization cycle; sensing a baseline concentration of the sterilant at a first set of environmental parameter values; detecting a real time change in the electrical characteristic of the sensing element as an indication of a new concentration of the sterilant at the first set of environmental parameter values; transmitting the value of the new concentration to the sterilizer control, and controlling the sterilant concentration in real time during the sterilization cycle in response to a signal from the sterilizer control system.

The method preferably includes the step of establishing a new baseline sterilant concentration value in response to a change in value of any one of the first set of environmental parameters during the sterilization cycle. The method further preferably includes the steps of maintaining the sterilant concentration value within the reference sterilant concentration range for a period of time sufficient to achieve sterilization and exhausting the sterilant from the sterilizer when sterilization is achieved.

The method preferably further includes the steps of providing a sensor probe external to the sterilizer, programming the sterilizer control system to store a predetermined sterilant concentration limit value, and stopping the admitting of sterilant into the sterilizer and/or exhausting sterilant from the sterilizer when the external sterilant concentration exceeds the predetermined concentration limit value.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

We claim:

1. A system for real-time monitoring and electronic control of the concentration of a liquid or gas sterilant or disinfectant chemical during a sterilization/disinfection cycle, comprising:

a sensor probe comprising a sensing element positioned in a sterilizer in fluid communication with a sterilant/disinfectant chemical for sensing therein a baseline concentration of the chemical at a first set of environmental parameter values, said element having a baseline electrical characteristic value at said baseline concentration, and a receiving unit electronically connected to the sensing element, the receiving unit being programmed to electronically store the baseline electrical characteristic value and to detect in real time a change in the electrical characteristic value of the sensing element as an indication of a second concentration of the chemical at the first set of environmental parameter values;

a control system;

a transmitting unit electronically connecting the receiving unit to the control system for real time transmitting to the control system of a value representing the second chemical concentration at the first set of environmental parameter values; and a process control unit in electronic communication with the control system for changing the chemical concentration in the chamber in response to a signal from the control system, wherein the control system is programmed to store a predetermined reference chemical concentration range at the first set of environmental parameter values; the control system is further programmed to receive a second concentration value and compare the second concentration value to the electronically stored reference concentration range; the control system is further programmed to indicate acceptable sterilization/disinfection conditions when the second chemical concentration value falls within the reference concentration range; and the control system is further programmed to signal the process control unit to change the sterilant\disinfectant chemical concentration when the second concentration value falls outside the reference concentration range.

2. The system of claim 1, wherein the set of environmental parameter values comprises a selection from the group consisting essentially of temperature, pressure, relative humidity, air flow velocity, an oxidizing substance concentration, and combinations thereof.

3. The system of claim 2, wherein the control system is further programmed to monitor the set of environmental parameter values during a sterilization/disinfection cycle and, when a parameter value changes, to signal the receiving unit to adjust the sensor system by recognizing and storing a new baseline sterilant/disinfectant chemical concentration value at the new set of environmental parameter values.

4. The system of claim 3, wherein the sterilant/disinfectant chemical concentration value is controlled and maintained within the reference concentration range for a period of time sufficient to achieve sterilization/disinfection.

5. The system of claim 1, wherein the electrical characteristic is capacitance.

6. The system of claim 1, wherein the electrical characteristic is resistance.

7. The system of claim 1, wherein the process control unit comprises a means to admit sterilant/disinfectant chemical into the chamber.

8. The system of claim 1, wherein the process control unit comprises a means to exhaust sterilant/disinfectant chemical from the chamber.

9. The system of claim 1, wherein the process control unit comprises a means to change an environmental parameter value.

10. The system of claim 1, wherein the sterilant/disinfectant chemical is selected from the group consisting essentially of ethylene oxide gas, liquid hydrogen peroxide, hydrogen peroxide gas, liquid formaldehyde, formaldehyde gas, liquid peroxygen compounds, gaseous peroxygen compounds, ozone, alcohol, glutaraldehyde, ammonia, and mixtures thereof.

11. The system of claim 1, further comprising a sensor probe comprising a sensing element in electronic communication with a receiving unit, said probe positioned externally to the sterilizer/disinfector, and a transmitting unit electronically connecting the receiving unit to the control system for real time transmitting to the control system of a value representing a sensed sterilant/disinfectant chemical concentration external to the sterilizer/disinfector, wherein the control system is further programmed to store a predetermined sterilant/disinfectant chemical concentration limit value and to signal the process control system to stop the sterilization/disinfection cycle and/or exhaust sterilant/disinfectant from the sterilizer/disinfector when the external concentration value exceeds the predetermined limit value.

12. A method for real-time monitoring and electronic control of the concentration of a liquid or gas chemical sterilant during a sterilization cycle performed in a sterilizer including (i) a sensor probe comprising a sensing element positioned in the sterilizer in fluid communication with a sterilant for sensing a concentration of the sterilant, said sensing element having an electrical characteristic, (ii) a receiving unit in electronic communication with the sensing element for real time detecting of a change in said electrical characteristic as an indication of a change in the sterilant concentration, (iii) a sterilizing control system in electronic communication with the receiving unit, and (iv) a process control unit in electronic communication with the sterilizer control system, said method comprising:

a exposing the sensor element to the sterilant during a sterilization cycle;

b reading an electronic concentration signal from the probe and electronically storing the read signal as a baseline concentration of a sterilant in the sterilizer at a first set of environmental parameter values;

c electronically monitoring the electronic concentration signal to monitor a real time change in the electrical characteristic of the sensing element as an indication of a second concentration of the sterilant at the first set of environmental parameter values;

d electronically transmitting in real time a value representing the second sterilant concentration at the first set of environmental parameter values; and e electronically controlling the sterilant concentration in real time during the sterilization cycle, f storing a predetermined reference sterilant concentration range at the first set of environmental parameter values;

g comparing the second concentration value to the stored reference concentration range;

h indicating acceptable sterilization conditions when the second sterilant concentration value falls within the reference second concentration range; and i signaling the process control unit to change the second sterilant concentration when the second concentration value falls outside the reference second concentration range.

13. The method of claim 12, further comprising the step of maintaining the sterilant concentration value within the reference sterilant concentration range for a period of time sufficient to achieve sterilization.

14. The method of claim 13, further comprising the step of exhausting the sterilant from the sterilizer when sterilization is achieved.

15. The method of claim 12, wherein the set of environmental parameter values comprises a selection from the group consisting essentially of temperature, pressure, relative humidity, air flow velocity, an oxidizing substance concentration, and combinations thereof.

16. A method for real-time monitoring and electronic control of the concentration of a liquid or gas chemical sterilant during a sterilization cycle in a sterilizer including (i) a sensor probe having a sensing element in fluid communication with a sterilant for sensing a concentration of the sterilant, said sensing element having an electrical characteristic, (ii) a receiving unit in electronic communication with the sensing element for real time detecting of a change in said electrical characteristic as an indication of a change in the sterilant concentration and (iii) a sterilizer control system and process control unit in electronic communication with the receiving unit, said method comprising:

a) electronically programming said sterilizer control system to store a predetermined reference sterilant concentration range at a first set of environmental parameter values;

b) electronically programming said sterilizer control system to receive a second concentration value and compare the second concentration value to the stored reference concentration range;

c) electronically programming said sterilizer control system to indicate acceptable sterilization conditions when the second sterilant concentration value falls within the reference concentration range;

d) electronically programming said sterilizer control system to signal the process control unit to change the second sterilant concentration when the second concentration value falls outside the reference concentration range; and the set of environmental parameter values comprises a selection from the group consisting essentially of temperature, pressure, relative humidity, air flow velocity, an oxidizing substance concentration, and combinations thereof;

e exposing the sensor element to the sterilant during a sterilization cycle;

f reading an electronic concentration signal from said sensor probe and electronically storing the read signal as a baseline concentration of a sterilant in the sterilizer at the first set of environmental parameter values;

g electronically monitoring the electronic concentration signal to monitor a real time change in the electrical characteristic of the sensing element as an indication of a second concentration of the sterilant at the first set of environmental parameter values;

h electronically transmitting in real time a value representing the second sterilant concentration at the first set of environmental parameter values;

i electronically controlling the sterilant concentration in real time during the sterilization cycle; and j establishing a new baseline sterilant concentration value in response to a change in value of any one of the first set of environmental parameters during a sterilization cycle.

17. The method of claim 12, wherein the electrical characteristic is capacitance.

18. The method of claim 12, wherein the electrical characteristic is resistance.

19. The method of claim 12, wherein the controlling comprises admitting sterilant into the chamber.

20. The method of claim 12, wherein the controlling comprises exhausting sterilant from the chamber.

21. The method of claim 12, wherein the controlling comprises changing an environmental parameter value.

22. The method of claim 12, wherein the sterilant is selected from the group consisting essentially of ethylene oxide gas, liquid hydrogen peroxide, hydrogen peroxide gas, liquid formaldehyde, formaldehyde gas, liquid peroxygen compounds, gaseous peroxygen compounds, ozone, and mixtures thereof.

23. A method for real-time monitoring and electronic control of the concentration of a liquid or gas chemical sterilant during a sterilization cycle conducted in a sterilizer including (i) a sensor probe having a sensing element positioned external to the sterilizer in fluid communication with a sterilant for sensing a concentration of the sterilant, said element having an electrical characteristic, said sensing element being in electronic communication with a receiving unit for real time detecting of a change in said electrical characteristic as an indication of a change in the sterilant concentration and (ii) a sterilizer control system and process control unit in electronic communication with the receiving unit, wherein the sterilizer control system is programmed to store a predetermined reference sterilant concentration range at a first set of environmental parameter values; the sterilizer control system is further programmed to receive a second concentration value and compare the second concentration value to the stored reference concentration range; the sterilizer control system is further programmed to indicate acceptable sterilization conditions when the second sterilant concentration value falls within the reference concentration range; and the sterilizer control system is further programmed to signal the process control unit to change the second sterilant concentration when the second concentration value falls outside the reference concentration range; said method comprising the steps of:

a) exposing the sensor element to the sterilant during a sterilization cycle;

b) reading an electronic concentration signal from said sensor probe and electronically storing the read signal as a baseline concentration of a sterilant in the sterilizer at the first set of environmental parameter values;

c) electronically monitoring the electronic concentration signal to monitor a real time change in the electrical characteristic of the sensing element as an indication of a second concentration of the sterilant at the first set of environmental parameter values;

d) electronically transmitting in real time a value representing the second sterilant concentration at the first set of environmental parameter values;

e) electronically controlling the sterilant concentration in real time during the sterilization cycle; and f) in the sterilizer control system, storing a predetermined sterilant concentration limit value, and stopping the admitting of sterilant into the sterilizer and/or exhausting sterilant from the sterilizer when the external sterilant concentration value exceeds the predetermined concentration limit value.

24. A method for real-time monitoring and electronic control of a concentration of a liquid or gaseous sterilant or disinfectant chemical during a sterilization/disinfection cycle, the method comprising:

reading an electronic concentration signal from a probe and electronically storing the read signal as a base line concentration of the chemical in a sterilization/disinfection chamber;

electronically calculating a current sterilant/disinfectant chemical concentration value from the stored base line concentration and the real-time change;

electronically comparing, with a controller computer, the current sterilant/disinfectant chemical concentration value to a previously determined and electronically stored reference concentration range;

generating an electrical signal indicating acceptable sterilization/disinfection conditions in response to the current concentration value falling with the reference concentration range; and generating an electronic control signal that causes a change in the sterilant/disinfectant chemical concentration within the sterilization/disinfection chamber in response to the current concentration value falling outside of the reference concentration range.

* * * * *